United States Patent
Cotterill et al.

(12)

(10) Patent No.: US 6,330,820 B1
(45) Date of Patent: Dec. 18, 2001

(54) FRICTION MATERIAL TESTING APPARATUS

(75) Inventors: Ronald I Cotterill; Kenneth Dunning, both of Chapel-en-le-Frith; James B Marshall, Dronfield; Alan Davenport, Chapel-en-le-Frith, all of (GB)

(73) Assignee: Federal-Mogul Friction Products Limited, Manchester (GB)

( * ) Notice: Subject to any disclaimer, the term of this patent is extended or adjusted under 35 U.S.C. 154(b) by 0 days.

(21) Appl. No.: 09/600,459

(22) PCT Filed: Jan. 18, 1999

(86) PCT No.: PCT/GB99/00159

§ 371 Date: Jul. 17, 2000

§ 102(e) Date: Jul. 17, 2000

(87) PCT Pub. No.: WO99/37993

PCT Pub. Date: Jul. 29, 1999

(30) Foreign Application Priority Data

Jan. 22, 1998 (GB) .................................................. 9801217

(51) Int. Cl.[7] .................................. G01N 3/56; G01L 5/28
(52) U.S. Cl. ........................................... 73/9; 73/7; 73/121
(58) Field of Search ................................. 73/121, 9, 125, 73/132, 10, 7; 192/12

(56) References Cited

U.S. PATENT DOCUMENTS

| | | | |
|---|---|---|---|
| 3,360,977 | * | 1/1968 | Herman ........................................ 73/9 |
| 3,852,993 | * | 12/1974 | Bronovets et al. ........................ 73/12 |
| 4,038,863 | * | 8/1977 | Mellor et al. ................................ 73/9 |
| 5,168,750 | * | 12/1992 | Kurtz ............................................ 73/132 |
| 5,685,193 | * | 11/1997 | Hurtubise et al. .................. 73/150 A |
| 5,689,058 | * | 11/1997 | Yuan ............................................. 73/9 |
| 5,697,472 | * | 12/1997 | Walker et al. .................. 188/1.11 W |

* cited by examiner

*Primary Examiner*—Hezron Williams
*Assistant Examiner*—Katina Wilson
(74) *Attorney, Agent, or Firm*—Thomas S. Baker, Jr.

(57) ABSTRACT

Apparatus 10 (FIG. 1), for testing samples of friction material 31, 32 in rubbing contact with a surface 33 of a rubbing element 34, comprises a table 12 for supporting the rubbing element and a load cell 16 for sensing the load imposed by the frictionally coupled rotating samples from which the coefficient of friction can be determined. To make the tests repeatable rapidly and with identical starting conditions cooling means 40 is interposed between the rubbing element and table. Cooling means 40 comprises a fluid cooled heat exchanger 41, conveniently cooled by local main supply water supplied at its natural temperature, and thermoelectric cooling means 75. The thermoelectric cooling means consists of an array of planar peltier cooling elements which develops a temperature gradient there across which, with reference to the heat exchanger temperature, is able to cool and re-cool the rubbing element to temperatures as low as −25° C. within a matter of minutes. To ensure the friction material and rubbing element are not contaminated by water condensed from the atmosphere an enclosure 60 is formed around them and kept at positive pressure by dry, inert argon gas.

20 Claims, 3 Drawing Sheets

FRICTION MATERIAL TESTING APPARATUS

Figure 1:
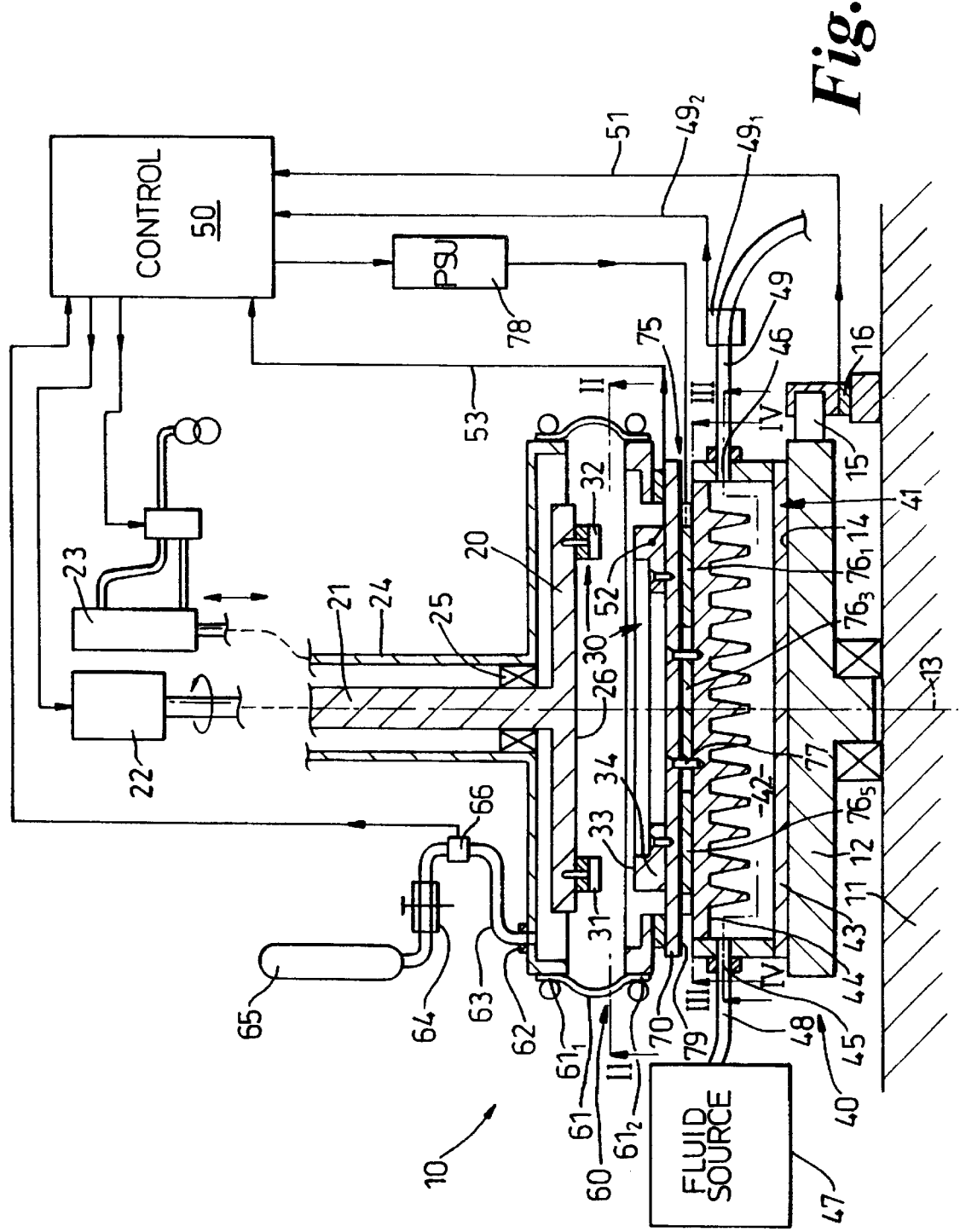

This invention relates to testing apparatus for friction materials used in brakes, clutches and the like and in particular relates to the testing the functioning of such materials within friction couples, that is, when pressed into rubbing engagement with a relatively moving rubbing element.

The invention relates to providing apparatus in which simple tests may be carried out repeatedly with minimal delay in substantially unvarying conditions It furthermore relates to apparatus capable of simulating friction couple operation where low, possibly sub-zero, conditions have to be repeatable and at a rate that also permits tests to be repeated with minimal delay.

It is known to test a friction material for vehicle braking systems prior to specifying its use by subjecting a relatively small sample of the material, typically less than 4 cm$^2$ in surface area, to a succession of simulated braking operations, within a friction couple, that is, by repeatedly bringing it to bear, under controlled 'braking pressure', against a relatively moving rubbing element of the material, usually a metal such as cast iron, used in the vehicle brake itself, to simulate said brake application, the consequential retardation forces it produces and frictional heat it generates. Because of the relatively small area of rubbing contact, the relative speed, braking application (bearing) pressure and retardation forces are correspondingly scaled down, and suitable for testing apparatus us ed within a workshop or laboratory environment.

It will be appreciated that as the frictional rubbing occurs between the friction material and rubbing element, heat is generated which raises the temperature of the rubbing element. Whereas in a vehicle braking system there is usually motion and infrequent brake applications which permit the heat within the rubbing element to dissipate, conditions are not so favourable within the climate of a workshop or laboratory, where the lack of such motion and the ambient temperature may also compromise the ability to simulate braking repeatedly within a practicably short time as the heat generated in each test must be dissipated before the same starting conditions are re-established for each subsequent test with the same friction material or a different friction material for comparative testing; that is, the duration of a test program is directly related to the speed at which initial temperature or hundreds of simulated braking operations, each of which may last only a few seconds, may become impracticable to conduct within a workshop or laboratory with known testing machines.

There also exists a requirement to simulate vehicle braking operation within an operating environment significantly below the freezing point of water. Such vehicle braking thus occurs in an atmosphere that is dry, in the sense that it contains no water in vapour or liquid form. However, this is less than trivial to achieve within the aforesaid workshop or laboratory environment, because of both the relatively high ambient temperature and atmospheric moisture in such environment, and the need to reproduce identical conditions at will.

Thus in respect of testing apparatus that simulates a friction couple by creating rubbing friction in order to test friction materials, whereas the apparatus may be of relatively simple form, the generation of frictional heat creates practical difficulties in reproducing conditions for performing such simulations in a commercially practicable manner. Analogous considerations apply also to friction materials used in non-vehicular brakes and in dry-plate clutch arrangements, and having regard to the above, it is an object of the present invention to provide a friction material testing arrangement of compact and simple construction that permits practicably rapid repetition of frictional rubbing operations with a friction couple. It is furthermore an object of the present invention to provide friction material testing apparatus of compact and simple construction that is capable, within a workshop or laboratory environment, of simulating frictional rubbing with a friction couple in subzero temperatures with commercially practicable repetition.

According to the present invention apparatus for testing the frictional behaviour of dry friction material in a friction couple with a relatively moving rubbing surface against which it is pressed repeatedly comprises the apparatus (i) an element carrier arranged to support a rubbing element of thermally conductive material, having a said rubbing surface, said element carrier being movable in the plane of the rubbing surface, (ii) sample carrier for at least one sample of said friction material, disposed facing said element carrier, one of said element and sample carriers comprising a table that is rotatable within limits of constraint and the other one of said carriers being rotatable with respect to the table, (iii) carrier drive means arranged to move said other one of the carriers and the friction couple component thereon orthogonal or parallel with respect to said table and the friction couple component thereon to make and break rubbing contact between the rubbing surface and each contacting sample and characterised by (iv) measuring means operable to sense the temperature of the rubbing element and, in response to friction between the rubbing surface and friction material, to limit rotation of the table and measure the force applied to said table by way of the rubbing element, (v) control means operable to control the carrier drive means to effect frictional coupling in response to the temperature of the rubbing element being below a predetermined trigger temperature, and (vi) cooling means operable to extract heat forcibly from the rubbing element to reduce it to said predetermined trigger temperature.

The cooling means may comprise heat exchanger means in which a fluid coolant forced to pass over a thermal conductor in a thermal conduction path including the rubbing element. Preferably such heat exchange means comprises a walled container having at least one wall in thermal contact with the rubbing element, inlet and outlet ports operable to admit and remove said fluid coolant and a source of said fluid coolant arranged to deliver it to the container inlet port at a predetermined rate.

The cooling means may also include thermoelectric cooling means having at least one thermoelectric cooling element disposed between, and in thermal contact with, the heat exchanger means and rubbing element, and power supply means arranged to provide a predetermined level of current to each thermoelectric cooling element.

Figure 2:
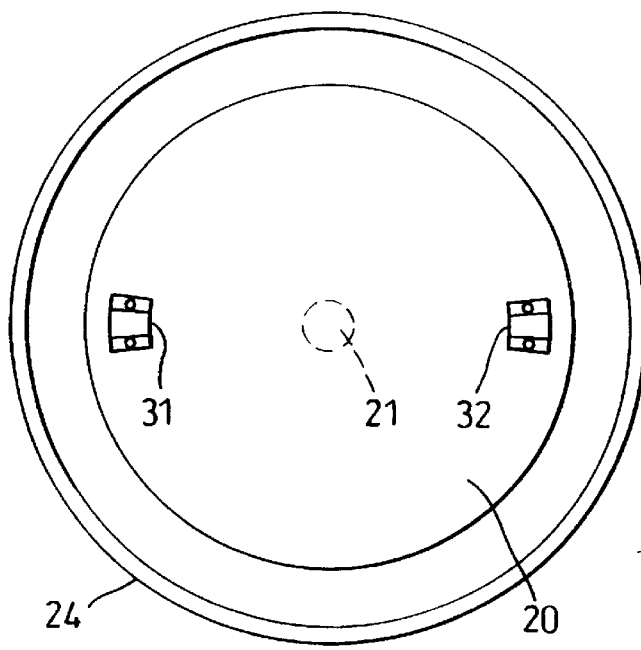
Figure 3:
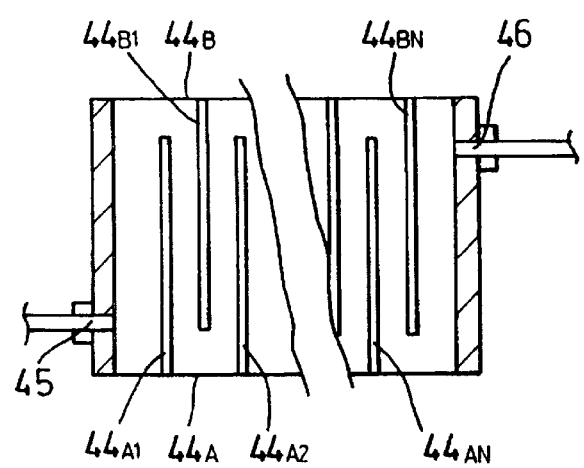
Figure 4:
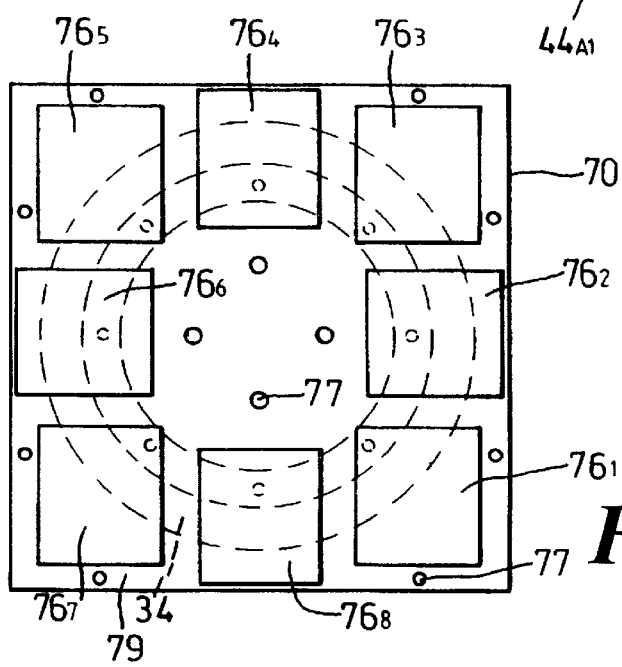
Figure 5:
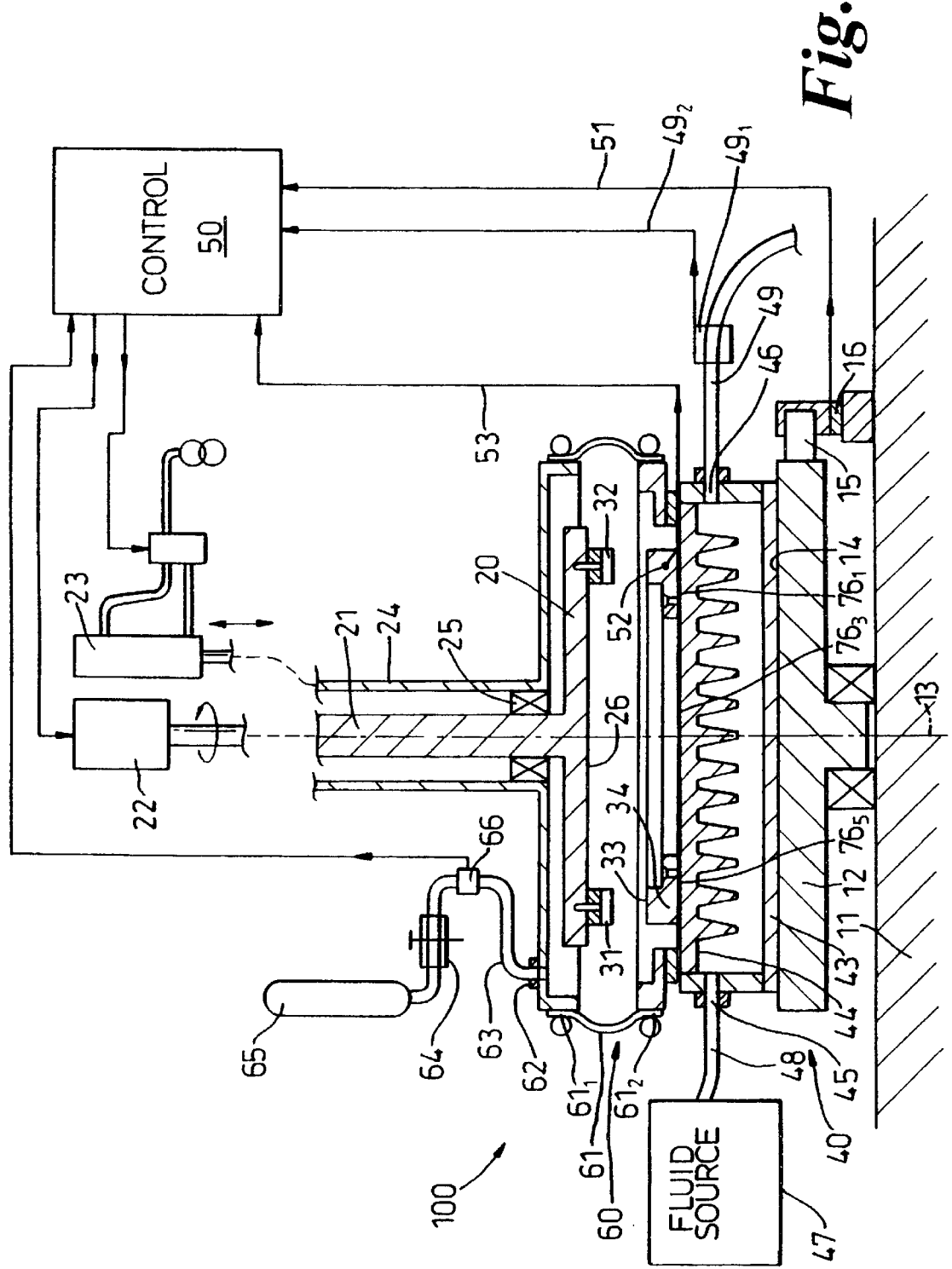

Embodiments of the present invention will now be described by way of example with reference to the accompanying drawings, in which:

FIG. 1 is a sectional elevation through friction material testing apparatus, in accordance with the present invention, in the form of a simulated braking arrangement comprising a rotatable carrier of friction material samples and a stationary rubbing element, and including cooling means for the rubbing element comprising fluid coolant heat exchanger means and thermoelectric cooling means, FIG. 2 is a cross-sectional view along the line II—II of FIG. 1 having two samples of friction material disposed on a rotatable sample carrier, FIG. 3 is a cross-sectional view along the line III—III of FIG. 1 showing the internal arrangement of the heat exchanger means, and disposition of the rubbing element in relation thereto, FIG. 4 is a cross-sectional view along the line IV—IV of FIG. 1 showing the disposition of the thermoelectric cooling means in relation to the rubbing element, and FIG. 5 is a sectional elevation through a simplified form of friction material testing apparatus, similar to FIG. 1 but in which the cooling means has no thermoelectric cooling means.

Referring to FIGS. 1 to 4, the test apparatus shown generally at 10 comprises a static machine bed 11 upon which is supported a table 12 that is rotatable about a substantially vertical axis 13. The table has a substantially horizontal upper surface 14 and a radially extending projection 15 which is disposed to engage with a force measuring device 16, such as a load cell. The projection does not have permanent contact with the device 16 but a small clearance with it such that if the table is driven to rotate about axis 13, the degree of free movement is small before impeded by abutment with the force measuring device. The force measured by the device is thus capable of representing a rotation torque acting on the table.

Concentric with, and disposed above, the table is a sample carrier 20 having a vertically extending drive shaft 21 which is rotatable about the vertical axis 13 by a motor 22 and reciprocable towards and away from the table by a ram 23. It will be understood that the motor may be driven by any suitable energy source and linked to the shaft by various ways. Likewise the ram may be fluid driven or mechanical, that is, formed by cam and/or geared coupling to the motor. As shown schematically in this embodiment the motor 22 is electrically driven and the ram 23 pneumatic.

The shaft 21 and sample carrier 20 is in part surrounded by a rotationally fixed shroud 24 which holds the shaft aligned and rotatable by way of bearings 25 or the like.

The sample carrier 20 overlies the table 12 and has a surface 26 facing towards the surface 14 of the table; the surfaces 26 and 14 carry the component parts of a friction couple, indicated generally at 30, comprising samples 31, 32 of a friction material and a rubbing surface 33 of an annular rubbing element 34, the friction material and rubbing element material being those to be employed in a proposed braking system but scaled down in dimensions. The rubbing element is cast iron.

The samples 31, 32 of friction material are secured to the surface 26 of the rotatable sample carrier and the rubbing element 34 is secured with respect to the surface 14 of table 12 by way of intervening cooling means indicated generally at 40, described fully below, the table comprising an element carrier.

In order to test the properties of the friction material in respect of its coefficient of friction and possibly wear rate or how the frictional coupling falls or fades as the frictional rubbing between samples and rubbing surface generates heat, the apparatus is provided with control means 50. The control means has outputs connected to the ram 23, to displace the sample carrier along the axis 13 and cause the samples 31 and 32 to bear against the rubbing surface with a predetermined pressure that simulates a braking pressure, such as the weight of the sample carrier and shaft, and connected to the drive motor 22 to rotate the sample carrier 20 with respect to the rubbing surface to simulate with the pressure, the frictional rubbing and retardation of brake application.

Such frictional rubbing couples the friction material to the rubbing element to rotate it and the table 12 upon which it is supported about the axis 13. However, the table 12 and rubbing member are prevented from significant rotation by the projection 15 and force measuring device 16, so that the load imposed on the device 16 is representative of the coefficient of friction that couples the driving and driven components of the friction couple. The force measuring device 16 provides electrical signals supplied to control means 50 by line 51 and/or to an external recording device (not shown).

The apparatus 10 also includes a temperature sensor 52 in thermal contact with the rubbing element and coupled to the control means by line 53. The temperature sensor is conveniently disposed adjacent the rubbing surface 33 and provides an immediate response to the temperature generated within the friction couple and independently of any thermal impedance of the rubbing element material.

The control means 50 is capable of being programmed to provide relative motion and simulated braking pressure between the components of the friction couple and to monitor the resultant coupled forces/torque and temperature rise repetitively. The components of the friction couple are separated from each other after a predetermined interval of rubbing, typically of the order of 10 to 15 sec, or after the temperature sensor has recorded a predetermined temperature, or rise in temperature, from an initial temperature that is conveniently called herein the trigger temperature, as desired, and are brought back into contact when the rubbing element returns to the trigger temperature. That is, to ensure that the starting conditions for each simulated braking operation are the same, it is necessary for the control means to ascertain from the temperature sensor that the rubbing element has cooled to said trigger temperature.

Clearly the rate at which frictionally generated heat is dissipated from the rubbing element governs the frequency with which such simulated braking operations can be repeated and to this end the cooling means 40 is provided to extract heat forcibly from the rubbing element to at least help reduce it to said predetermined triggering temperature.

The cooling means comprises heat exchanger means 41 in the form of a walled container 42, having a first wall 43 supported on, and secured to, the surface 14 of the table 12 and a second wall 44 in indirect thermal contact with the rubbing member by way of thermoelectric cooling means 75 described fully below . The heat exchanger container also has an inlet port 45 and an outlet port 46 disposed at opposite sides of the container and arranged respectively to admit a fluid coolant from source 47 by way of pipe 48 and to remove it by way of pipe 49. The source 47 and/or valve means (not shown) is arranged to cause the fluid coolant to be delivered to the inlet port at a predetermined rate that is chosen to give a suitable rate of heat transfer between the second container wall and the fluid within the container, and there is also provided a flow switch $49_1$ which is coupled to the control means by line $49_2$ to act to inhibit operation in the absence of adequate fluid flow.

Preferably all walls of the container are thermally conductive and in contact with the fluid coolant, but particularly the second wall 44, and to this end. the heat exchanger means is used with the first wall 43 forming a substantially horizontal base to the container and the inlet and outlet ports displaced above that base so that when the fluid coolant is a liquid, a non-draining pool of liquid forms in the container. Such a pool of liquid, if harmless environmentally, such as water, can act in an emergency if the supply fails to dissipate consider able heat by evaporation and coincidentally give a visual signal by emission of steam.

To maximise heat exchange efficiency the second wall 44 has a plurality of 2N integral fins $44_{A1}$, $44_{A2}$ ... $44_{AN}$, $44_{B1}$, $44_{B2}$ ... $44_{BN}$, extending into the container between the inlet and outlet ports.

Referring to FIG. 3, each of said fins extends along said wall 44 substantially between opposite edges $44_A$ and $44_B$ thereof and substantially orthogonally to the direction between the inlet and outlet ports 45 and 46.

The N fins $44_{A1}$, $44_{A2}$ ... $44_{AN}$ each extend from edge $44_A$ but are truncated and terminate short of wall edge $44_B$ and the N fins $44_{B1}$, $44_{B2}$ ... $44_{BN}$ similarly extend from edge $44_B$ but terminate short of wall end $44_A$, the alternately disposed fins defining a serpentine path between the inlet and outlet ports between, and by way of the truncated ends of, adjacent fins. The fins may extend into the chamber almost into contact with the opposite, first, wall 43 but at least to an extent that has them immersed in a said pool of liquid coolant.

As indicated above, one particular requirement to be met is the simulated braking by the friction couple in an operating environment which is both below the normal ambient environmental temperature of the workshop or laboratory in which the apparatus is situated and below a temperature at which atmospheric moisture can condense and effectively contaminate the components of the friction couple.

In such circumstances, not only is there a requirement for the rubbing element to be cooled to such a low trigger temperature, in a practicably short time between each of the repeated simulated braking tests in which heat is generated, it must be achievable with no contamination of the components of the friction couple, nor their working interrelationship, by atmospheric water.

The cooling means 40 includes enclosure means 60 for the components of the friction couple in the form of an envelope or tent-like sleeve 61 of flexible material having poor thermal conductivity. The sleeve surrounds, and has one end $61_1$ clamped to the shroud 24 and extends axially from it towards the heat exchanger means where the other end $61_2$ is similarly secured to define an enclosure whose side wall is flexible to permit deformation upon bringing together the samples and rubbing member. A duct 62 through the shroud 24 has connected thereto one end of a flexible pipe 63 the other end of which is connected to a pressure regulator 64 of a compressed gas source 65. The gas is preferably argon, having suitably poor thermal conductivity and being inert.

Notwithstanding the quality of clamping between the sleeve and the shroud and heat exchanger means there is inevitable leakage between the enclosure and the surrounding environment, for example, along the sample carrier drive shaft, and to this end the gas pressure regulator 64 is arranged to provide gas at a pressure slightly above ambient atmospheric pressure, that is, a pressure of the order of 1.1 to 1.2 bar, which is sufficient to maintaining a positive pressure differential between the enclosure atmosphere and surrounding environment. Such flexible side wall defined by the sleeve is also useful in providing a quick visual indication that such a suitable positive pressure differential exists by virtue of the tendency for the wall to bulge when such differential is established. If desired a sensor 66 may be associated with the pressure regulator 64 (or even the enclosure 60 itself) to detect that the appropriate atmospheric conditions exist within the enclosure and be coupled to the control means 50 to inhibit the simulated braking operations in the absence of a suitable pressure differential.

As mentioned above one particular testing requirement to be met is the simulated braking by a friction couple in a simulated operating environment which is significantly below the freezing point of water, possibly lower than −25° C. Notwithstanding the exact trigger temperature to which it is necessary to cool the rubbing element between each simulated braking operation, it must be achieved in a practicably short time and cost-effectively. It will be appreciated that there is a practical difficulty in reducing the temperature of the rubbing member significantly and rapidly by way of a simple heat exchanger means 41, which has an intrinsically large thermal inertia, without recourse to elaborate arrangements in respect of the fluid coolant.

The cooling means 40 further includes a first, flat-faced thermally conductive body, comprising the second wall 44 of the heat exchanger container and a second, flat-faced thermally conductive body 70, such as a plate of aluminium or like metal, upon which is supported the rubbing element 34, and thermoelectric cooling means, indicated generally at 75, which has an intrinsically low thermal inertia. The thermoelectric cooling means comprises a plurality of thermoelectric (Peltier) cooling elements $76_1$, $76_2$, $76_3$ ... sandwiched between the first and second bodies 44 and 70 by clamping means 77 in the form of bolts extending between the bodies, and power supply means 78 arranged to provide a predetermined level of current to each thermoelectric cooling element under the control of the control means 50.

In this specific embodiment, and as seen from FIG. 4, the thermoelectric cooling means comprises an array of substantially planar thermoelectric cooling elements sandwiched between the first and second bodies 44 and 70 in approximate alignment with the annular rubbing element. Suitable thermoelectric cooling elements are of the DuraTEC™ series produced by Marlow Industries Inc., Dallas, Tex., USA. Elements having a manufacturers list number D T 12-6 measure some 44×40×4 mm and have flat ceramic faces suitable for clamping between the two bodies with only a small increase in separation of the rubbing element from the heat exchanger means.

Because the faces of the thermoelectric elements are ceramic and flat the surfaces of the bodies 44 and 70 must be correspondingly flat, and remain flat when clamped together to sandwich the elements, to make good thermal contact. This may be achieved principally by forming such bodies of metal plates which have significant thickness to avoid deformation upon clamping, but because of slight variations in thickness between individual elements, clamping together of the bodies may not result in proper thermal contact with each and every element and to this end a resiliently compressible thermally conductive membrane 79 of the type commercially available for use with semiconductor device heat sinks is interposed between the second body 70 and the thermoelectric cooling elements. The remaining space between the second body 70 and first body 44 is filled with moisture excluding wax, gel or like material.

It will be understood that when each of the thermoelectric elements $76_1$ ... has a current passed therethrough a temperature difference is generated between the faces of the device as a function of the current. The face adjacent the second body cools and extracts heat from the second body and rubbing member whereas the face adjacent the first body heats as a function of both that extracted heat and the electrical power consumed within the device itself. That heat is extracted by the heat exchanger means. The thermal inertia of the heat exchanger means, in practice, the temperature of the second body/rubbing element to be defined relative to the heat exchanger fluid temperature.

The manufacturer quotes for each element having the above manufacturer's list number a heat pump capacity of 54 W, maximum temperature difference ΔT between faces of 68° C., maximum current of 5.6 A and maximum voltage of 14.6 V.

In this embodiment, an array of eight such devices $76_1$–$76_8$ is used with the elements connected in series such that each passes a current of approximately 4 A at 14V. The heat exchanger means is, as mentioned above, connected to the local water supply main to receive water as the fluid coolant at approximately 11° C. and at a supply rate of approximately 2 liter/min thereby establishing a nearly constant temperature for the first body 44 of the thermoelectric cooling means that is usually lower than room temperature.

The second plate is of aluminium and has dimensions of 160×160×12 mm and the annular rubbing element has an outside diameter of 135 mm, a radial thickness of 13 mm, half of which is the rubbing surface 33, and an axial thickness of 6.5 mm and weight 172 gramme, being of cast iron.

It was found that having cooled the first body 44 to approximately 11° C. by the passage of water coolant through the heat exchanger means, a rubbing element initially at +20° C. was cooled by the action of the thermoelectric cooling means in accordance with Table 1.

TABLE 1

| Rubbing member temperature (° C.) | Thermoelectric cooling time (Sec.) |
|---|---|
| +20 | 0 |
| +10 | 35 |
| +5 | 60 |
| 0 | 90 |
| −5 | 120 |
| −10 | 180 |
| −15 | 270 |
| −20 | 420 |
| −23 | 600 |
| −25 | 850 |

One simulated braking test comprised initiating rubbing contact at a trigger temperature of −23° C. and maintaining contact for a period of about 15 sec. Before breaking contact, the force measuring device 16 during that time determining the frictionally coupled load that defines the coefficient of friction between the samples and rubbing surface. The rubbing element was then cooled until the same trigger temperature was reached and frictional contact re-established. This cycle was repeated a number of times for each friction material and for different friction materials.

It was found that if the thermoelectric cooling means was kept operating throughout the simulated braking operation, with heat being generated in the rubbing element, the rise in temperature at the end of the simulation was approximately −10° C. The time required to cool the rubbing element from −10° C to −23° C. was only about 60 sec. and thereby determined the interval between tests.

Whereas Table 1 suggests that such re-cooling of the rubbing element should take of the order of 420 sec (=600−180), that assumes that the whole rubbing element/second body 70 is raised to the same temperature as the rubbing surface 33. It will be appreciated that the temperature of the rubbing surface (where the sensor is located) rises to a peak within a few seconds and before the heat can be distributed throughout the bulk of the rubbing element and second body. The amount of heat generated corresponds to a much smaller overall temperature rise to be countered by the thermoelectric cooling means and thus a re-distribution of, and extraction of, heat is achieved in this much shorter time.

It was also found that if the thermoelectric cooling means was operated only after the frictional rubbing had ceased, the rubbing member had risen to a measured temperature of about +10° C. and the time taken to re-cool the rubbing element to −23° C. was about 90 sec compared with the 565 sec (=600−35) which the table predicts.

The above values are quoted as examples only and may be expected to vary from one apparatus and location to another. However, the speed and simplicity of establishing such conditions repeatably is demonstrated thereby. Which operating strategy is used will depend upon whether each simulated braking test is based upon a fixed braking interval or upon temperatures generated.

It will be appreciated that the rubbing element may be cooled to a somewhat lower trigger temperature by increasing the cooling time interval, involving no additional changes other than to increase the overall time for performing a series of simulated braking tests.

Alternatively, the temperature difference between the surfaces of the thermoelectric cooling elements may be increased by having thermoelectric cooling elements of higher electrical power consumption in conjunction with heat transfer within the heat exchanger means by the internal design of heat transfer surfaces, flow rate, the temperature at which the fluid coolant is supplied and/or the nature of the fluid coolant itself. As mentioned above, there are economic and environmental advantages for using water as the fluid coolant and such water or water containing anti-freeze additives may be supplied to the heat exchanger means precooled to a temperature closer to, or even below 0° C. However, any other liquid having suitable thermal conductivity and freezing point may be employed or the fluid coolant may be a gas which is caused to flow by the fins of the heat exchanger means (as illustrated or suitably modified), either a re-circulated and externally cooled thermally conductive gas or air, the latter being possibly being atmospheric air blown through the heat exchanger and expelled.

It will be seen that the compact thermoelectric cooling means, notwithstanding the generation of heat by its own power consumption, enables a rubbing element temperature significantly below 0° C. to be achieved not only cost effectively but also rapidly and in turn permits simulated braking tests to be repeated sufficiently quickly for such repetitive test to be practicable within an industrial environment.

It will be appreciated that the cooling means may be less elaborate than shown in FIGS. 1 to 4, depending upon the stringency of the testing required, particularly the trigger temperature. For example, in the thermoelectric cooling means the second body 70 may be omitted if it is practicable to clamp the rubbing element directly to the first body, that is, the wall 44 of the heat exchanger container. Similarly, the first body may be formed by a plate (not shown) discrete from the container wall but which is coupled thereto, making the thermoelectric cooling means more readily separable as a unit from the heat exchanger means.

If it is not required to effect extreme cooling and/or rate of cooling of the rubbing element, the thermoelectric cooling means may be omitted altogether, as illustrated in apparatus 100 in FIG. 5, wherein the cooling means 40 differs from the above described cooling means 40 by such omission and the rubbing element 34 is coupled directly to the heat exchanger means and through which a suitable fluid coolant, at suitable supply temperature, is passed. As all of the integers of the embodiment are present in apparatus 10, like reference numbers are used and no further detailed description given.

It will be appreciated that in the embodiment 100 the enclosure means 60 may also be omitted if the degree of cooling required does not reduce the friction couple components below the dew point of the ambient environment of the workshop or laboratory in which the apparatus is situated.

Whereas the above description has concentrated upon a simulated braking test, it will be appreciated that an analogous test may be performed, with less heat generation but possibly with the requirement for low trigger temperature, for friction couple components of a dry clutch arrangement.

In the above, it will be appreciated that as heat is generated in, and requires to be dissipated from, the rubbing element, the apparatus is arranged such that the samples of friction material move relative to a substantially stationary rubbing element, easing the making of the various electrical and fluid connections to the cooling means. It will be understood that if desired the friction material samples may be supported on the table 12 (which then becomes the sample carrier) and the rubbing element may be rotated on an element carrier that is the equivalent of the sample carrier 20, provided suitable provision is made with respect to cooling means which would have to be at least, in part, rotatable with the rubbing element.

It will be appreciated that the dimensions, shape and material of the rubbing element may be varied from those mentioned above. Likewise, the dimensions and number of samples of friction material may also be varied as a matter of choice.

What is claimed is:

1. Apparatus for testing the frictional behaviour of dry friction material in a friction couple with a relatively moving rubbing surface against which it is pressed repeatedly, comprising:

(i) an element carrier arranged to support a rubbing element of thermally conducted material, having a said rubbing surface, said element carrier being movable in the plane of the rubbing surface, (ii) a sample carrier for at least one sample of said friction material, disposed facing said element carrier, one of said element and sample carriers comprising a table that is rotatable within limits of constraint and the other one of said carriers being rotatable with respect to the table, (iii) carrier drive means arranged to move said other one of the carriers and the friction couple component thereon orthogonal and parallel with respect to said table and the friction couple component thereon to make and break rubbing contact between the rubbing surface and each contacting sample, (iv) measuring means operable to sense the temperature of the rubbing element and, in response to friction between the rubbing surface and friction material, to limit rotation of the table and measure the force applied to said table by way of the rubbing element.

(v) control means operable to control the carrier drive means to effect frictional coupling in response to the temperature of the rubbing element being below a predetermined trigger temperature, and (vi) cooling means operable to extract heat forcibly from the rubbing element to reduce it to said predetermined trigger temperature.

2. Apparatus as claimed in claim 1 in which the cooling means comprises heat exchanger means in which a fluid coolant is forced to pass over a thermal conductor in a thermal conductor path including the rubbing element.

3. Apparatus as claimed in claim 2 in which the heat exchange means comprises a walled container having at least one wall in thermal contact with the rubbing element, inlet and outlet ports operable to admit and remove said fluid coolant respectively and a source of said fluid coolant arranged to deliver it to the container inlet port at a predetermined rate.

4. Apparatus as claimed in claim 3 in which at least one wall of the container has a plurality of fins extending therefrom into the container between the inlet and outlet ports.

5. Apparatus as claimed in claim 4 in which each of said fins extends along said one wall substantially between the opposite edges thereof and substantially orthogonally to the direction between said inlet and outlet ports, but wherein successive fins are truncated clear of the edge of said wall at opposite ends thereof alternately to define a serpentine path between the inlet and outlet ports between and by way of the truncated ends of said fins.

6. Apparatus as claimed in claim 1 in which the container is arranged to retain therein a pool of liquid.

7. Apparatus as claimed in claim 2 in which the fluid coolant is a liquid.

8. Apparatus as claimed in claim 6 in which the liquid is water.

9. Apparatus as claimed in claim 3 in which the fluid coolant is water, the source is the local cold water supply main and the water is supplied to the container at the ambient temperature of said supply main.

10. Apparatus as claimed in claim 1 in which the cooling means includes enclosure means operable to define an atmosphere for the rubbing element and friction material sample that is substantially free of water.

11. Apparatus as claimed in claim 10 in which the enclosure means comprises a flexible envelope, arranged to extend between and around the rubbing element and friction material sample, and a supply of gas, substantially dry and unreactive with any component of the friction couple, arranged to supply said gas to the envelope to maintain a pressure therein in excess of ambient atmospheric pressure.

12. Apparatus as claimed in claim 11 in which the gas is argon.

13. Apparatus as claimed in claim 12 in which the cooling means includes thermoelectric cooling means having at least one thermoelectric cooling element disposed between and in thermal contact with the heat exchanger means and rubbing element and power supply means arranged to provide a predetermined level of current to each thermoelectric cooling element.

14. Apparatus as claimed in claim 13 in which the thermoelectric cooling means includes a first body comprising, or thermally coupled to, the heat exchange means and a second body comprising, or thermally coupled to, the rubbing element, and clamping means arranged to clamp the first and second bodies together to sandwich each thermoelectric cooling element therebetween.

15. Apparatus as claimed in claim 14 in which the second body comprises a substantially flat-faced, rigid metal plate arranged to support the rubbing element against one face thereof and to bear against each said thermoelectric element with the other face.

16. Apparatus as claimed in claim 14 including a layer of resiliently compressible thermally conductive material disposed between said second body and the surface of each thermoelectric element.

17. Apparatus as claimed in claim 14 in which the thermoelectric cooling means comprises a plurality of thermoelectric cooling elements disposed in a substantially planar array substantially in alignment with the rubbing element.

18. Apparatus as claimed in claim 13 in which the thermoelectric cooling means is arranged to define, absent engagement between rubbing and friction elements, a temperature difference between the fluid coolant, supply temperature and disengaged rubbing element greater than 20° C.

19. Apparatus as claimed in claim 18 in which the thermoelectric cooling means is arranged to define a temperature difference between the fluid coolant, supply temperature and disengaged rubbing element in the range 30° C. to 50° C.

20. Apparatus as claimed in claim 18 in which the cooling means includes enclosure means, operable to define an atmosphere for the rubbing element and friction material sample that is substantially free of water, comprising a flexible envelope, arranged to extend between and around the rubbing element and friction material sample, and a supply of gas, substantially dry and unreactive with any component of the friction couple, arranged to supply said gas to the envelope to maintain a pressure therein in excess of ambient atmospheric pressure and in which the thermoelectric cooling means is arranged to define a said temperature difference for a rubbing element in less than 10 minutes.

* * * * *